United States Patent [19]

Schiraldi et al.

[11] Patent Number: 5,099,039
[45] Date of Patent: Mar. 24, 1992

[54] PRODUCTION OF THE FROM 1,4-BUTANEDIOL USING A POLYBENZIMIDAZOLE CATALYST

[75] Inventors: David A. Schiraldi, Pineville, N.C.; Bennett C. Ward, New Providence, N.J.

[73] Assignee: Hoechst Celanese Corp., Somerville, N.J.

[21] Appl. No.: 609,562

[22] Filed: Nov. 6, 1990

[51] Int. Cl.$^5$ .................................. C07D 307/08
[52] U.S. Cl. ......................................... 549/509
[58] Field of Search .............................. 549/509

[56] References Cited

U.S. PATENT DOCUMENTS

| | | | |
|---|---|---|---|
| 3,467,679 | 9/1969 | Rogers | 549/509 |
| 3,726,905 | 4/1973 | Coates et al. | 549/509 |
| 4,093,633 | 6/1978 | Tanabe et al. | 549/509 |
| 4,196,130 | 4/1980 | Huchler et al. | 549/509 |
| 4,203,908 | 5/1980 | Mueller et al. | 549/509 |
| 4,904,806 | 2/1990 | Hoelderich et al. | 549/509 |

Primary Examiner—C. Warren Ivy
Assistant Examiner—Amelia A. Owens
Attorney, Agent, or Firm—Joseph M. Mazzarese

[57] ABSTRACT

A process for converting 1,4-butanediol to tetrahydrofuran using polybenzimidazole to catalyze the reaction. The conversion is accomplished by heating the 1,4-butanediol in the presence of the PBI. The THF product may be distilled from the reaction solution as an azeotrope with water. To function as the catalyst, the PBI must first be pre-treated with a strong aqueous acid such as sulfuric acid. The catalyst may be in the form of microporous resin beads, hollow fibers, or other forms of PBI. This process exhibits a high selectivity for producing THF without side reactions.

7 Claims, 2 Drawing Sheets

PRODUCTION OF THE FROM 1,4-BUTANEDIOL USING A POLYBENZIMIDAZOLE CATALYST

This invention relates to a process for the production of tetrahydrofuran ("THF") from 1,4-butanediol, and particularly to such a process wherein polybenzimidazole ("PBI") catalyzes the conversion of the 1,4-butanediol to THF.

BACKGROUND OF THE INVENTION

More than half of the THF produced worldwide is manufactured from 1,4-butanediol. It is well-known that THF forms as a result of the dehydration and cyclization of 1,4-butanediol. However, this reaction proceeds very slowly in the absence of a catalyst.

A variety of catalysts are known to promote the conversion of 1,4-butanediol to tetrahydrofuran, including sulfuric acid, oxalic acid, phosphoric acid, copper sulphate, magnesium chloride, zinc chloride, a number of metal oxides and phosphates, sulfonic acid cation exchange resins, acidic nuclear sulfonated cross-linked aromatic hydrocarbon resins, and aluminum hydride-impregnated silica. Processes for the catalytic production of THF from 1,4-butanediol are described in U.S. Pat. Nos. 4,380,657, 4,196,130, 3,726,905 and 3,467,679, the disclosures of which are herein incorporated by reference.

Common disadvantages associated with the catalysts currently used in processes for making THF include limited selectivity, high energy requirements, high cost, corrosiveness, short catalyst lifetime, and/or loss of materials or product.

For example, strong acids, such as sulfuric acid, have the disadvantage of being highly corrosive. This is especially detrimental to metal reaction vessels.

Some other catalysts, such as the cation exchange resins, operate only at very high temperatures. High temperatures increase energy costs as well as promoting the undesirable degradation of the catalyst, the product, and/or the starting material. These resin catalysts often have relatively short lifetimes.

Presently, a common commercial method for THF production involves heating 1,4-butanediol in the presence of sulfuric or phosphoric acid to temperatures exceeding 270° C. at elevated pressures. This process tends to rapidly corrode reaction vessels, and requires a great deal of energy. Under these conditions, a THF product selectivity of 90-99% is usually obtained; a number of by-products form during the reaction. An additional procedure may be needed to remove these by-products.

SUMMARY OF THE INVENTION

Figure 1:
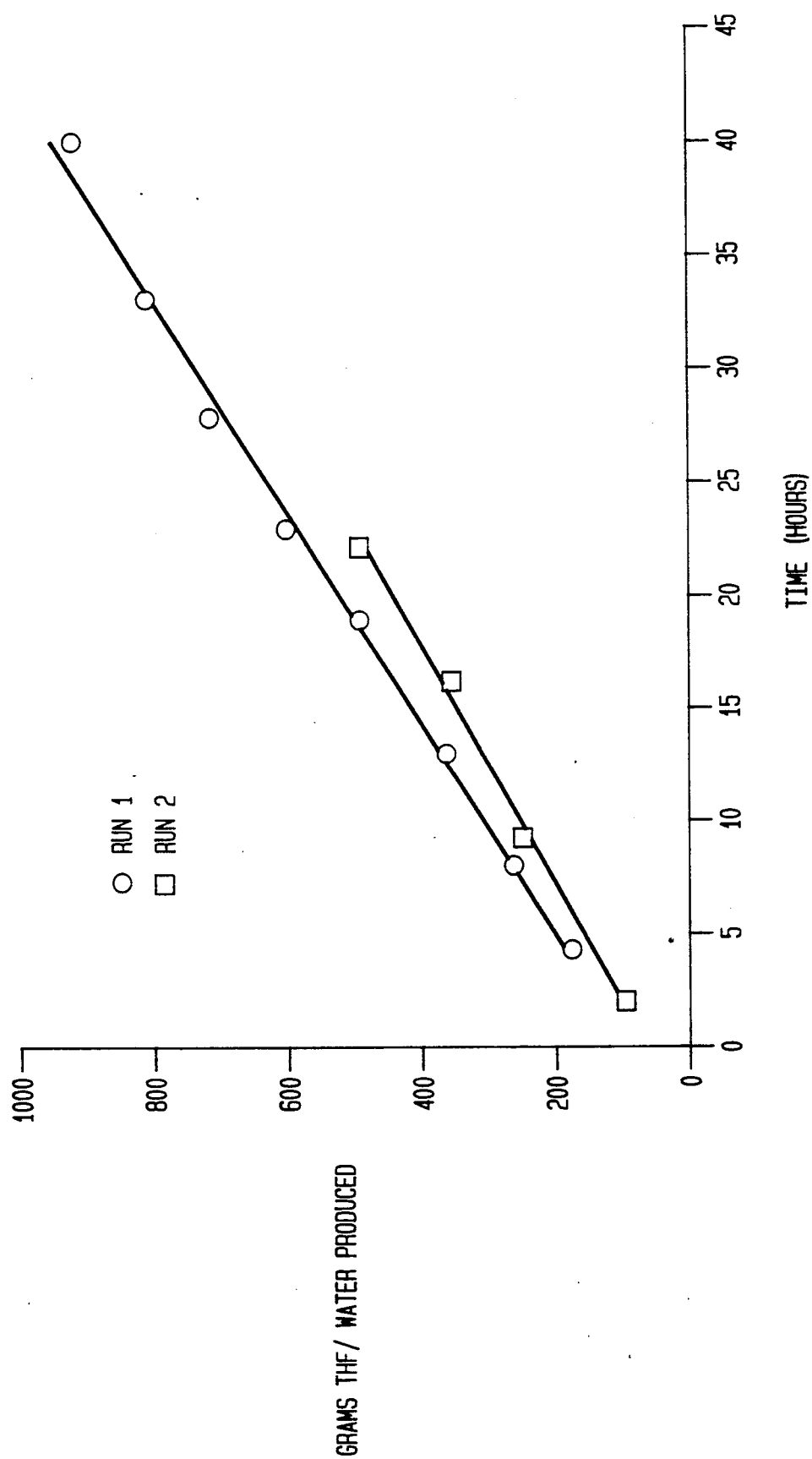
FIG. 1 is a plot of the amount of THF/water produced against reaction time for two separate runs using a PBI catalyst according to the present invention.

The present invention is a process for converting 1,4-butanediol to tetrahydrofuran using polybenzimidazole to catalyze the reaction. This transformation is accomplished by heating the 1,4-butanediol in the presence of the PBI. The THF product may be distilled from the reaction solution.

The PBI catalyst of this invention is in the protonated or acidic form, having been pre-treated with a strong aqueous acid such as sulfuric acid. Pre-treated PBI microporous resin beads, or other forms of PBI, may be used in this invention.

It is an object of the present invention to provide a novel catalyst for converting 1,4-butanediol to THF.

It is also an object of the present invention to provide a non-corrosive catalyst that rapidly and economically converts 1,4-butanediol to THF and that does not readily degrade.

It is another object of this invention to provide a process for making THF without forming a significant amount of by-products.

It is a further object of the present invention to provide a process and a catalyst for converting 1,4-butanediol to THF at relatively low or moderate temperatures.

These and other objects of the present invention will be apparent to those skilled in the art from the following detailed description and the appended claims and Figures.

DETAILED DESCRIPTION OF THE PREFERRED EMBODIMENTS

According to the present invention, 1,4-butanediol is heated in the presence of polybenzimidazole (acid form) whereupon the 1,4-butanediol molecule loses a water molecule and forms the cyclic compound tetrahydrofuran. A mixture of water and THF is distilled from the reaction mixture.

The invention may be practiced as either a batch, continuous, or semi-continuous process. Typically, the temperatures used range between about 60-63° C. (the boiling point of the THF:water 94:6 azeotrope) and about 220° C. The latter temperature is close to the boiling point of the reactant, 1,4-butanediol. PBI is stable at much higher temperatures, however, so the reaction may be run under pressure at temperatures at least as high as 250° C. Lower temperatures may also be used if the distillation is performed under reduced pressure. However, at very low temperatures the reaction rate may be unacceptably slow.

It is preferred to run the reaction at atmospheric pressure within an approximate temperature range of 100-220° C., more preferably within a range of about 120-200° C., and most preferably within a range of about 125-150° C. However, the pressure may be higher or lower than atmospheric pressure.

It is desirable to use a combination of temperature and pressure such that the reactant's vapor pressure is below the reaction pressure while the vapor pressure of the THF-water azeotrope at least equals the reaction pressure; this combination prevents the reactant from vaporizing while facilitating the distillation of the azeotrope. Those skilled in the art will know how to adjust the temperature and pressure to achieve this result. The choice of reaction conditions will be influenced by the desired reaction rate. For example, although a vacuum distillation at temperatures well below 60° C. is possible, it would be wise to use a temperature high enough to drive the reaction at a desirably rapid rate.

The preferred embodiments of this invention combine the reaction step with a distillation separation step. However, it will be understood that this is not a necessity. A temperature-pressure combination could be chosen such that the 1,4-butanediol dehydrates and condenses to form the product, but the product remains in solution; in this case, the THF could be separated from the solution subsequently, either by distillation or by other known methods of separation.

It is believed that the one-step reaction-distillation is most efficient for several reasons, including the following: elimination of the product from the reaction mixture drives the reaction equilibrium toward formation of more THF; the entire process proceeds more rapidly when done in one step; and, the energy used to drive the reaction also is used to drive the separation of the product from the reactant mixture.

The reactant, 1,4-butanediol, is widely available commercially. It may be produced by a number of methods, including reacting formaldehyde with acetylene, hydrolyzing N,N'-dinitro-1,4-butanediamine with dilute sulfuric acid, reducing succinic esters or succinaldehyde, and hydrogenating butynediol. Commercially, substantial amounts of 1,4-butanediol are used to produce THF, polymers, and butyrolactone.

The preferred polybenzimidazole, poly[2,2,'-(m-phenylene)-5,5'-bibenzimidazole], is commercially available from the Hoechst Celanese Corporation (Charlotte, N.C.). Polybenzimidazoles are a class of linear polymers having repeat units containing the benzimidazole moiety:

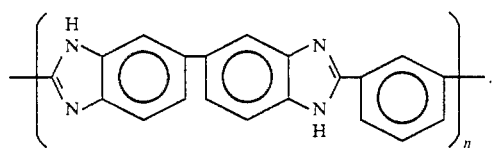
(I)

These compounds are nonflammable and may be formed into fibers, films, and membranes having outstanding thermal, physical, and chemical stability. Processes for their production are disclosed, for example, in U.S. Reissue Pat. No. 26,065 and U.S. Pat. Nos. 3,313,783, 3,509,108, 3,555,389, 3,433,772, 3,408,336, 3,549,603, 3,708,439, 4,154,919, and 4,312,976, the disclosures of which are herein incorporated by reference.

Polybenzimidazoles are prepared conventionally by the condensation of tetraamino compounds with dicarboxylic acids (or esters or halide salts thereof). For example, poly[2,2'-(m-phenylene)-5,5'-bibenzimidazole] may be prepared by reacting diphenyl isophthalate with 3,3',4,4'-tetraaminobiphenyl:

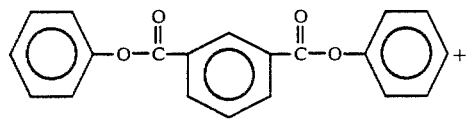
diphenyl isophthalate

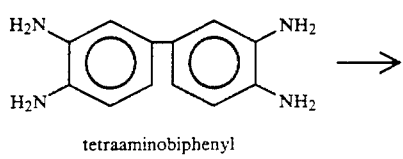
tetraaminobiphenyl

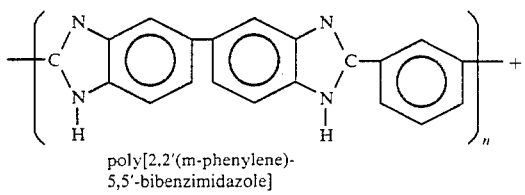
poly[2,2'(m-phenylene)-5,5'-bibenzimidazole]

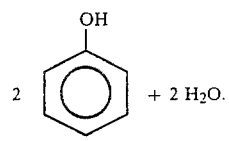
+ 2 H₂O.

More generally, U.S. Pat. No. 2,895,948 teaches the following condensation reaction for making polybenzimidazole:

(III)

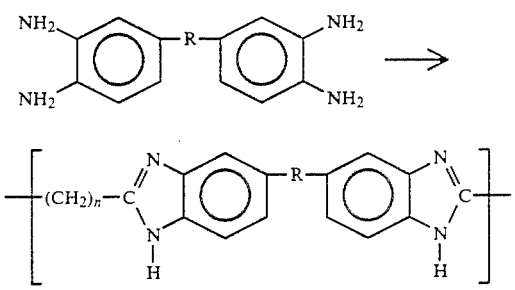

wherein R is a group selected from the class consisting of diphenyl bonds and divalent radicals, and n is an integer from 4 to 8. Other examples of conventional processes are disclosed in U.S. Pat. Nos. 4,814,530, 4,431,796, and 4,414,383.

The polymerization of PBI may be accomplished in several ways, such as in polyphosphoric acid or a hot molten nonsolvent such as sulfolane or diphenyl sulfone. Melt solid state polymerization is the commercially practical route.

PBI may be produced in many forms, including solid and hollow fibers, films and membranes, microporous beads, molded articles, and the like. Although PBI may be used in virtually any form to catalyze the production of THF in accordance with the present invention, microporous resin beads are preferred.

PBI may be converted from solution to microporous beads, fibers, or other physical forms, by well-known methods. For example, the solution may be sprayed through fine holes to form round, liquid aerosol particles which can be cooled to form microporous beads. The solution may also be spun into fibers using a commercial spinning apparatus. Such techniques are not unique to PBI, but have been applied to a variety of different polymers for many years. See, A. Buckley, et al., "Polybenzimidazoles", *Encyclopedia Of Polym. Sci. Eng.*, Mark, Bikales, Overberger, & Menges, Eds., Vol. 11, pp.572–601 (1988).

Regardless of the physical form or the exact chemical composition of the PBI used in this invention, to obtain the desired catalytic activity it is necessary to pretreat the PBI with a strong acid, e.g. sulfuric acid, to convert the polymer into the protonated (acid) form. This is a simple procedure well-known to those skilled in the art.

Polybenzimidazoles are known for their high temperature stability, nonflammability, and high chemical resistance. In contrast to the acid resins known to catalyze the production of THF, PBI has a significantly longer catalyst lifetime. Furthermore, PBI is capable of catalyzing the production of THF from 1,4-butanediol at relatively mild temperatures, although it is also well-suited for use at temperatures as high as about 250° C. or higher for extended periods. PBI also is not corrosive or harmful to reaction vessels.

Unlike other catalysts, the PBI-catalyzed production of THF according to this invention proceeds without any significant by-product formation or side reactions. This high selectivity makes the process more efficient and simplifies product purification. In the preferred embodiments of this process an azeotropic mixture of about 94% THF and about 6% water is distilled from the reaction vessel. The water may be separated from the THF by well-known methods. For example, desiccants such as calcium chloride, or azeotropic distillation (e.g. using benzene), may be used to remove the water.

The process for preparing THF according to the present invention has the additional advantage that catalyst and reactant losses due to the purging of reaction tars and unwanted salts is minimized compared to many other catalysts. This saves time and expense, and also allows a greater rate of production of THF by reducing system down time.

The following Examples are presented for the purpose of illustrating the invention; however, the invention is not limited to the embodiments illustrated.

EXAMPLE I

PBI microporous resin beads about 50–500 microns in diameter were treated with sulfuric acid and then washed with deionized water until neutral. The resin was then treated with 3% HCl, the aqueous acid was filtered off, and the beads were again washed with deionized water until the effluent had a pH of at least 4. The resin was then oven-dried at 120° C. for 14 hours.

EXAMPLE II

Five grams of the microporous PBI resin from Example I and 500 grams of 1,4-butanediol were combined in a one liter round-bottom flask equipped with a Claisen distillation head and condenser. The reaction flask was heated to 130° C. An azeotropic mixture containing 94% THF and 6% water began distilling overhead. The run was continued for 40 hours with periodic addition of more 1,4-butanediol to maintain the original liquid level to within about 100 milliliters.

Figure 2:
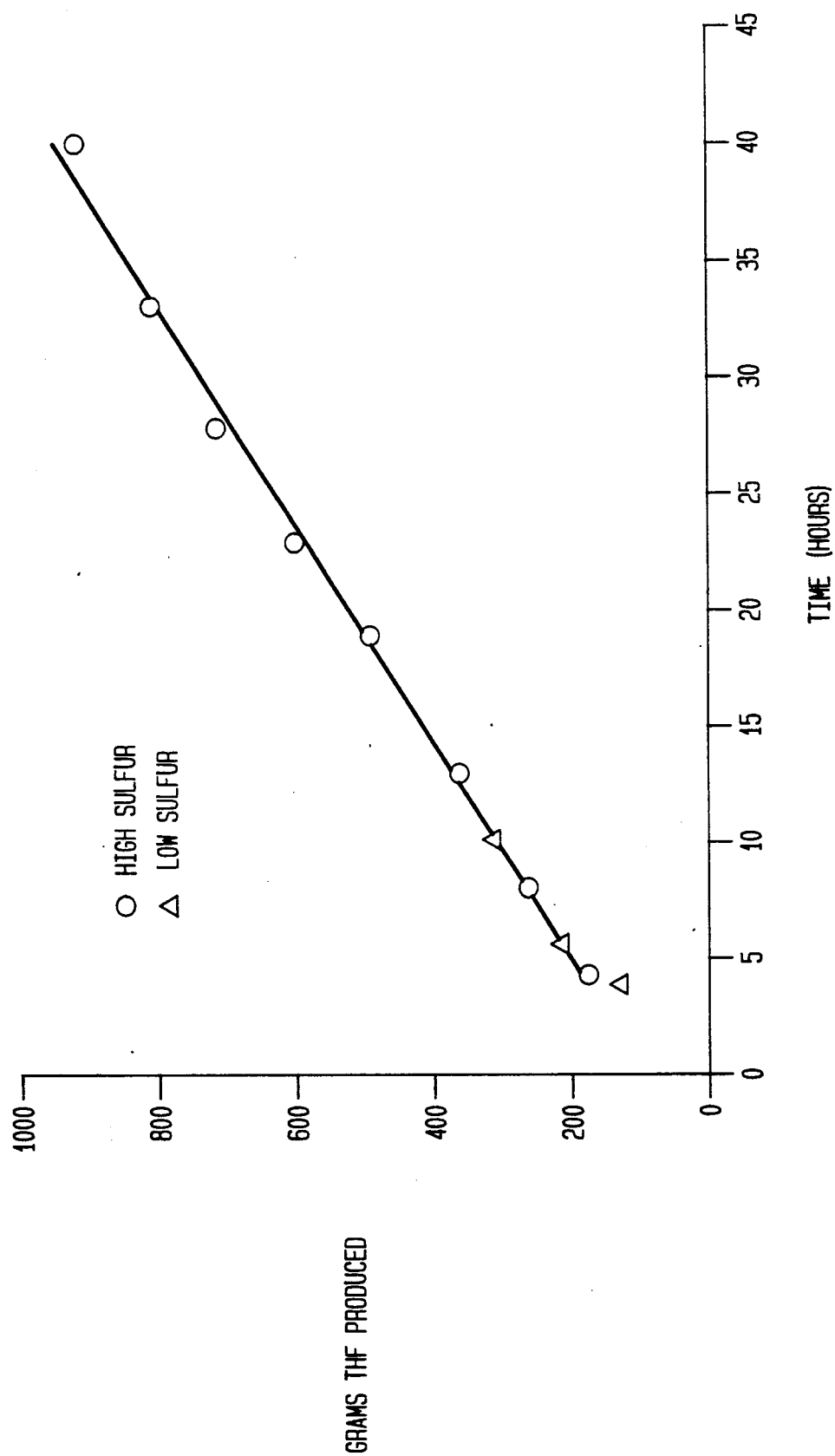
FIG. 2 is a plot of the grams of THF produced against reaction time for two different PBI catalysts of the present invention, one having a low sulfur content and the other a high sulfur content.

A total of 913 grams of distillate was collected. FIG. 1 shows the distillate collected over time for this run, which was designated "Run 1". FIG. 2 shows the grams of THF collected over time under the designation "high sulfur" to distinguish the PBI catalyst used in this Example from that of Example IV, which had a lower sulfur content. Analysis of the resin used in this Example showed a sulfur content of 3.0%.

During long-term trial no catalyst deactivization was observed over 40 hours of operation. Visual and electron microscope examination showed no noticeable PBI resin particle damage or generation of fines.

Analysis of the reaction products showed only THF and water in the distillate. Analysis of the reactant mixture showed only THF, water, reactant, catalyst and trace by-products and impurities (no more than 1%). Overall THF selectivity was found to be much greater than 99%.

EXAMPLE III

The catalyst of Example II was washed with 150 milliliters of deionized water, air dried for three hours, and recharged to a clean one liter flask. The experiment described in Example II was repeated for 22.25 hours. An additional 489 grams of distillate was collected. FIG. 1 shows the distillate collected over time for this run, which was designated "Run 2".

The rate of THF production was slightly less than in Example II, but the difference was small enough to be attributed to experimental error.

The catalyst was analyzed both before and after use, and the results are shown in Table I:

TABLE I

|  | Combustion Sulfur % | ESCA Surface Sulfur % | Surface Area (m$^2$/g) |
| --- | --- | --- | --- |
| Before Use | 3.0 | 13.6 | 8.9 |
| After Use | 2.2 | 7.8 | 10.9 |

EXAMPLE IV

The experiment conducted in Example II was repeated, except that a low sulfur PBI resin was used and the run was ended after 10 hours. The product generated and collected is shown in FIG. 2 under the designation "low sulfur". These results show that the catalytic activity of the PBI is not dependent on its sulfur content. This conclusion is further supported by the results of Example III wherein the catalyst had significantly lower sulfur content than it had prior to use, yet the THF production was not significantly less than in Example II.

EXAMPLE V

Four experiments were performed: one using no catalyst; a second using the PBI catalyst described in Example II; a third using a commercially available acidic resin catalyst called Dowex 50W-X8; and a fourth using sulfuric acid to catalyze the reaction.

In each case, 150 grams of 1,4-butanediol and 2 grams of catalyst (if used) were combined in a 250 ml round bottom flask equipped with a Claisen distillation head and condenser. The reaction flask was heated to 125° C. for 3 hours and as product was formed 94:6 THF:water azeotrope was distilled overhead and collected.

The overhead product and the remaining reaction mixture were analyzed. As shown in Table II, below, the PBI catalyst increased the reaction rate 50-fold compared to using no catalyst. The other catalysts produced THF 2–3 times faster than the PBI, but also generated a number of by-products; the PBI showed excellent THF selectivity.

Visual inspection of the catalysts after three hours of reaction revealed no change in the PBI, but significant changes in the Dowex. This is not surprising, since temperatures above about 100° C. can damage Dowex and similar resins, whereas PBI is known to have superior thermal stability and can withstand much higher temperatures.

TABLE II

|  | No Catalyst | PBI | Dowex | Sulfuric Acid |
| --- | --- | --- | --- | --- |
| Relative Reaction | 0.02 | 1 | 2.6 | 3.0 |

TABLE II-continued

|  | No Catalyst | PBI | Dowex | Sulfuric Acid |
|---|---|---|---|---|
| Rate (rate of THF production) |  |  |  |  |
| Number of Products | 1 | 1 | >10 | >10 |

EXAMPLE VI

Ten grams of sulfuric acid-treated hollow PBI fiber and 800 milliliters of 1,4-butanediol are combined in a two liter reaction vessel equipped with a distillation head, condenser, and collection vessel. The entire reaction-distillation system is kept under a nitrogen pressure of two atmospheres. The vessel is heated to 235° C., driving an azeotropic distillate of THF and water into the collection vessel. The temperature is maintained until the desired amount of distillate is collected.

EXAMPLE VII

Seven grams of microporous PBI resin beads prepared as in Example I are poured onto the bottom of a one-liter reaction vessel having a fluid inlet and a fluid overflow outlet near the top, and fitted with a distillation head and a condenser. The PBI catalyst is covered with about 300 milliliters of 1,4-butanediol and heated to 210° C. Additional 1,4-butanediol flows continuously into the vessel through the inlet at a rate of about 10 ml/min. Any reactant overflowing through the outlet is recycled through the inlet. An azeotropic mixture of THF and water distills overhead. The reaction is run continuously for a period of six days.

Many variations of the present invention will be apparent to those skilled in the art from the above description and the appended claims. The present invention includes all variations within the scope of the appended claims.

We claim:

1. A process for converting 1,4-butanediol to tetrahydrofuran comprising the steps of:
    combining a quantity of 1,4-butanediol with a polybenzimidazole catalyst consisting essentially of poly[2,2'-(m-phenylene)-5,5'-bibenzimidazole] to form a reaction mixture, said polybenzimidazole having been pre-treated with a strong acid; and,
    heating said mixture to convert said 1,4-butanediol to tetrahydrofuran and water.

2. A process according to claim 1 wherein said mixture is heated to a temperature between about 60° C. and about 220° C.

3. A process according to claim 1 wherein said mixture is heated to a temperature between about 100° C. and about 200° C.

4. A process according to claim 1 wherein said mixture is heated to a temperature between about 220° C. and about 250° C.

5. A process according to claim 1 further comprising the step of distilling said tetrahydrofuran from said reaction mixture, said tetrahydrofuran being distilled as a tetrahydrofuran-water azeotrope.

6. A process according to claim 5 wherein said heating step and said distillation step are performed simultaneously.

7. A process for producing tetrahydrofuran from 1,4-butanediol comprising the steps of:
    combining a quantity of 1,4-butanediol with a polybenzimidazole catalyst consisting essentially of poly[2,2'-(m-phenylene)-5,5'-bibenzimidazole] to form a reaction mixture, said polybenzimidazole having been pre-treated with a strong acid;
    heating said mixture at approximately atmospheric pressure to a temperature in the approximate range of 125-150° C. to convert said 1,4-butanediol to tetrahydrofuran and water, producing an azeotropic tetrahydrofuran-water product vapor; and,
    during said heating step, condensing and collecting said tetrahydrofuran-water product vapor.

* * * * *